(12) United States Patent
Aharoni et al.

(10) Patent No.: US 7,776,087 B2
(45) Date of Patent: Aug. 17, 2010

(54) INTRAOCULAR IMPLANTS

(75) Inventors: Eli Aharoni, Tel Aviv (IL); Yossi Gross, Moshav Mazor (IL)

(73) Assignee: Visioncare Ophthalmic Technologies Inc., Saratoga, CA (US)

(*) Notice: Subject to any disclaimer, the term of this patent is extended or adjusted under 35 U.S.C. 154(b) by 1163 days.

(21) Appl. No.: 11/069,581

(22) Filed: Mar. 1, 2005

(65) Prior Publication Data
US 2005/0209691 A1 Sep. 22, 2005

Related U.S. Application Data

(63) Continuation-in-part of application No. 10/321,793, filed on Dec. 17, 2002, now Pat. No. 7,001,427.

(51) Int. Cl.
*A61F 2/16* (2006.01)
(52) U.S. Cl. .......................... 623/6.11; 623/4.1; 607/54
(58) Field of Classification Search ................. 623/4.1, 623/6.11, 6.34, 6.63; 607/54
See application file for complete search history.

(56) References Cited

U.S. PATENT DOCUMENTS

| | | | |
|---|---|---|---|
| 3,515,461 A | 6/1970 | Rayces et al. | |
| 4,056,855 A | 11/1977 | Kelman | |
| 4,074,368 A | 2/1978 | Levy, Jr. et al. | |
| 4,463,458 A | 8/1984 | Seidner | |
| 4,527,294 A * | 7/1985 | Heslin ........................ | 623/6.12 |
| 4,581,031 A | 4/1986 | Koziol et al. | |
| 4,596,578 A | 6/1986 | Kelman | |
| 4,666,446 A | 5/1987 | Koziol et al. | |
| 4,710,197 A * | 12/1987 | Donn et al. ................. | 623/6.11 |
| 4,731,078 A * | 3/1988 | Stoy et al. ................... | 623/6.13 |
| 4,743,254 A | 5/1988 | Davenport | |
| 4,833,890 A * | 5/1989 | Kelman ...................... | 623/6.17 |
| 4,892,543 A | 1/1990 | Turley | |
| 4,911,714 A * | 3/1990 | Poley ......................... | 623/6.18 |
| 4,911,715 A * | 3/1990 | Kelman ...................... | 623/6.17 |
| 5,016,633 A * | 5/1991 | Chow .......................... | 607/53 |
| 5,026,396 A | 6/1991 | Darin | |
| 5,044,743 A | 9/1991 | Ting | |
| 5,108,429 A | 4/1992 | Wiley | |
| 5,222,981 A | 6/1993 | Werblin | |
| 5,354,335 A * | 10/1994 | Lipshitz et al. ............. | 623/6.13 |

(Continued)

FOREIGN PATENT DOCUMENTS

DE 34 28 895 A1 2/1986

(Continued)

OTHER PUBLICATIONS

Abstract of FR 2666735 published Mar. 20, 1992.*

(Continued)

*Primary Examiner*—Paul Prebilic
(74) *Attorney, Agent, or Firm*—Fish & Richardson P.C.

(57) ABSTRACT

An intraocular implant including a sealed capsule adapted for intraocular placement upstream of a retina, an electronic display located within the sealed capsule, electronic circuitry located within the sealed capsule for operating the electronic display, the electronic circuitry and the electronic display operative to selectably provide multiple display options, the multiple display options including allowing at least some light from the outside to pass through the electronic display and focusing optics located within the sealed capsule.

22 Claims, 11 Drawing Sheets

U.S. PATENT DOCUMENTS

| | | | |
|---|---|---|---|
| 5,391,202 A | | 2/1995 | Lipshitz et al. |
| 5,397,350 A * | | 3/1995 | Chow et al. .................. 623/6.63 |
| 5,405,387 A * | | 4/1995 | Sodero ........................ 623/6.13 |
| 5,628,798 A | | 5/1997 | Eggleston et al. |
| 5,653,751 A * | | 8/1997 | Samiy et al. ................ 623/6.63 |
| 5,814,103 A | | 9/1998 | Lipshitz et al. |
| 5,876,442 A | | 3/1999 | Lipshitz et al. |
| 5,928,283 A | | 7/1999 | Gross et al. |
| 5,964,802 A | | 10/1999 | Anello et al. |
| 6,007,579 A | | 12/1999 | Lipshitz et al. |
| 6,066,171 A | | 5/2000 | Lipshitz et al. |
| 6,197,057 B1 | | 3/2001 | Peyman et al. |
| 6,358,280 B1 * | | 3/2002 | Herrick ....................... 623/6.26 |
| 6,400,989 B1 * | | 6/2002 | Eckmiller ..................... 607/54 |
| 6,569,199 B1 | | 5/2003 | Dotan |
| 6,596,026 B1 | | 7/2003 | Gross et al. |
| 6,638,304 B2 | | 10/2003 | Azar |
| 6,847,847 B2 * | | 1/2005 | Nisch et al. ................... 607/54 |
| 6,849,090 B2 * | | 2/2005 | Nigam ........................ 623/5.13 |
| 6,902,577 B2 | | 6/2005 | Lipshitz et al. |
| 6,913,620 B2 | | 7/2005 | Lipshitz et al. |
| 7,001,427 B2 * | | 2/2006 | Aharoni et al. ............... 623/4.1 |
| 7,008,448 B2 | | 3/2006 | Lipshitz et al. |
| 7,079,900 B2 * | | 7/2006 | Greenburg et al. ............ 607/54 |
| 7,276,080 B2 | | 10/2007 | Murakami et al. |
| 2002/0143395 A1 * | | 10/2002 | Skottun ....................... 623/6.34 |
| 2002/0173846 A1 | | 11/2002 | Blake et al. |
| 2003/0060881 A1 * | | 3/2003 | Glick et al. ................. 623/6.37 |
| 2003/0078656 A1 * | | 4/2003 | Nguyen ....................... 623/6.37 |
| 2003/0105522 A1 * | | 6/2003 | Glazier ....................... 623/6.13 |
| 2003/0187502 A1 | | 10/2003 | Lipshitz |
| 2003/0187503 A1 | | 10/2003 | Lipshitz et al. |
| 2004/0117011 A1 * | | 6/2004 | Aharoni et al. ............. 623/6.11 |
| 2004/0148022 A1 | | 7/2004 | Eggleston |
| 2004/0236421 A1 | | 11/2004 | Lipshitz et al. |
| 2005/0065602 A1 * | | 3/2005 | Aharoni et al. ............. 623/6.22 |
| 2005/0071002 A1 * | | 3/2005 | Glazier ....................... 623/6.13 |
| 2005/0090875 A1 * | | 4/2005 | Palanker et al. ............... 607/54 |
| 2005/0154457 A1 * | | 7/2005 | Aharoni et al. ............. 623/6.35 |
| 2005/0222860 A1 * | | 10/2005 | Kawaoka et al. ................ 705/1 |

FOREIGN PATENT DOCUMENTS

| | | |
|---|---|---|
| DE | 195 01 444 A1 | 7/1996 |
| DE | 19501444 A1 | 7/1996 |
| EP | 0 099 641 | 2/1984 |
| EP | 0162573 | 11/1985 |
| EP | 0242043 | 10/1987 |
| EP | 0 897 702 A2 | 2/1999 |
| EP | 1438930 | 7/2004 |
| EP | 1475055 | 11/2004 |
| GB | 877083 | 9/1961 |
| WO | WO-83/01566 A1 | 5/1983 |
| WO | WO-88/06430 | 9/1988 |
| WO | WO-94/07435 A1 | 4/1994 |
| WO | WO-0004849 | 2/2000 |
| WO | WO-00/38593 A1 | 7/2000 |

OTHER PUBLICATIONS

An Office Action dated Jan. 31, 2009, which issued during the prosecution of Applicant's U.S. Appl. No. 11/420,327.

An Office Action dated Jan. 20, 2009, which issued during the prosecution of Applicant's Japanese Patent Application No. 2004-7118.

An International Search Report dated Feb. 26, 2007, which issued during the prosecution of Applicant's PCT Patent Application No. PCT/IL06/00873.

U.S. Appl. No. 10/321,793, filed Dec. 17, 2002, entitled: "Intraocular Implants".

An Office Action dated Sep. 8, 2009, which issued during prosecution of Applicant's Canadian Patent Application No. 2,455,076.

An Office Action dated Sep. 8, 2009, which issued during the prosecution of Applicant's Japanese Patent Application No. 2004-560169.

* cited by examiner

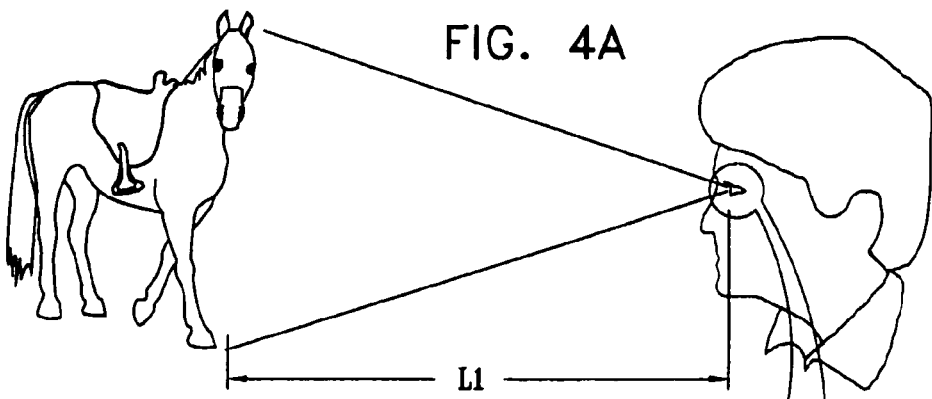
FIG. 4A
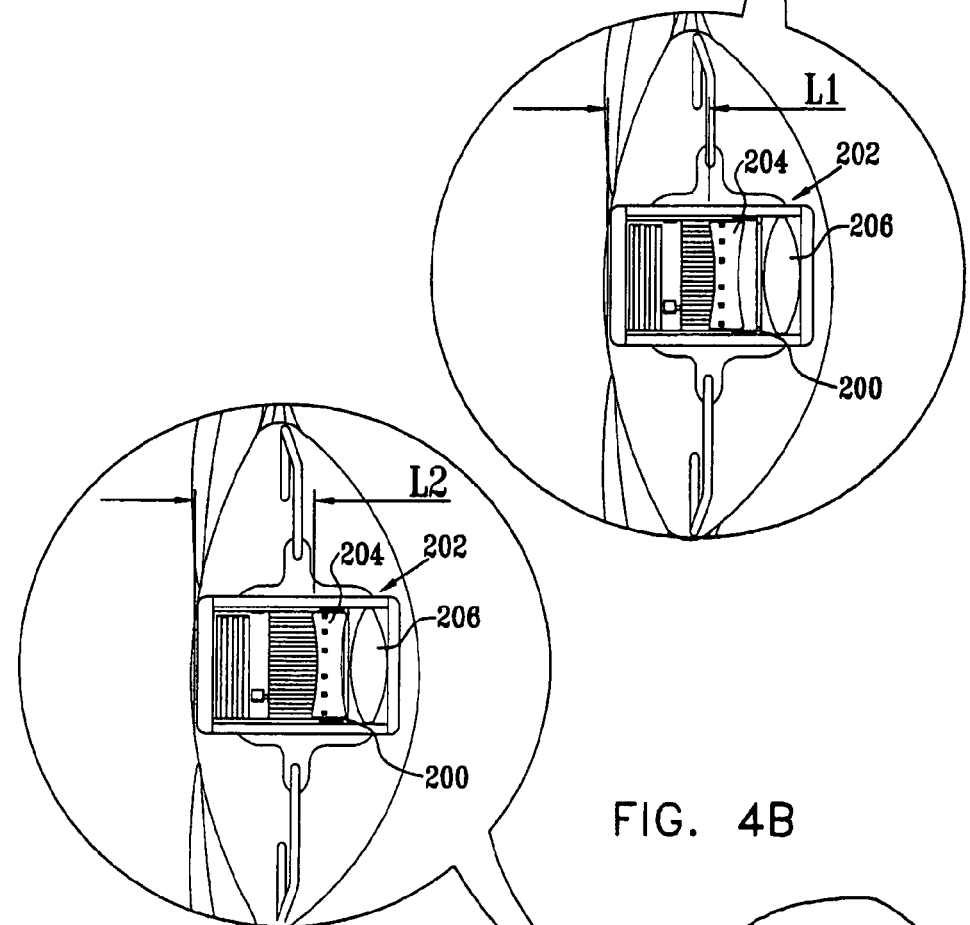
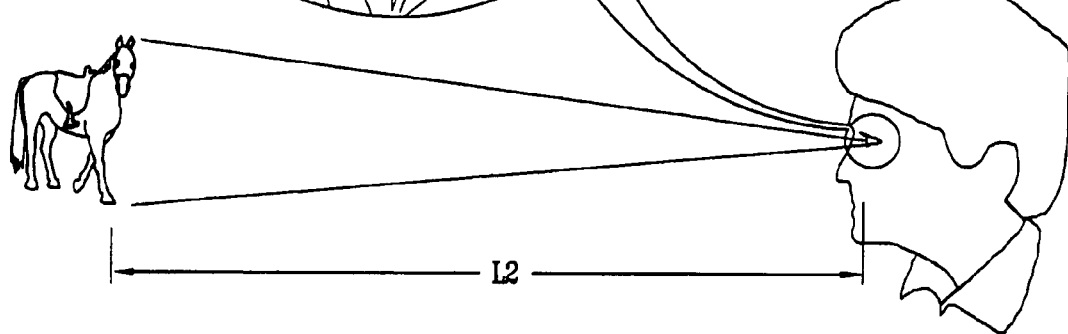
FIG. 4B

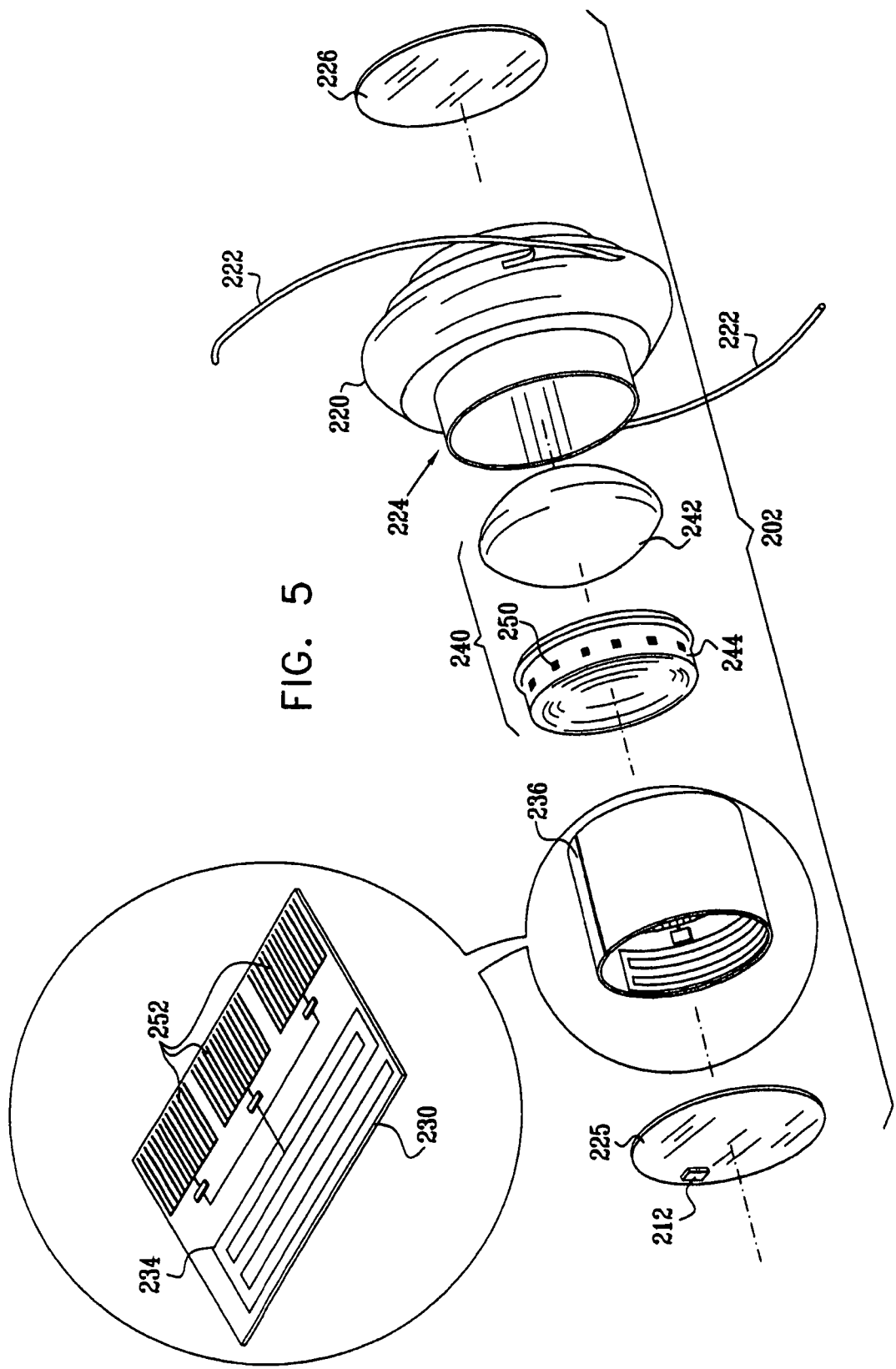

INTRAOCULAR IMPLANTS

REFERENCE TO CO-PENDING APPLICATIONS

This application is a continuation-in-part of U.S. application Ser. No. 10/321,793, filed Dec. 17, 2002, titled "Intraocular Implants" (now U.S. Pat. No. 7,001,427), the contents of which are incorporated by reference.

Applicants also make reference to the following co-pending U.S. Patent Applications, the disclosures of which are hereby incorporated by reference:

U.S. application Ser. No. 10/342,160, filed Jan. 14, 2003 (now U.S. Pat. No 6,972,032), entitled "Intraocular Lens Implant" and U.S. application Ser. No. 10/489,388, filed Mar. 11, 2004, entitled "Intraocular Implants."

FIELD OF THE INVENTION

The present invention relates to ocular implants generally and more particularly to intraocular implants.

BACKGROUND OF THE INVENTION

The following patent publications are believed to represent the current state of the art:

U.S. Pat. Nos. 5,354,335; 5,814,103; 5,876,442; 5,928,283; 6,007,579; 6,066,171; 5,653,751; 6,596,026; 6,569,199; 6,464,725; 5,391,202; 5,384,606; 4,074,368; 4,994,082; 5,628,798; 5,222,981; 4,172,297; 5,769,890; 4,892,543; 4,373,218; 4,968,127; 4,759,761; 4,976,732 and 5,769,889;

Published U.S. Application 2001/018,612;

Published PCT Applications WO 94/07,435; WO 00/38593 and WO 83/01566;

Foreign Patent Publications DE 4,403,326; EP 1,092,402; EP 0,419,740; GB 2,181,355; EP 0,897,702; EP 0,212,616; DE 3,428,895 and DE 19,501,444.

SUMMARY OF THE INVENTION

The present invention seeks to provide an intraocular implant with multiple viewing options.

There is thus provided in accordance with a preferred embodiment of the present invention an intraocular implant including a sealed capsule adapted for intraocular placement upstream of a retina, an electronic display located within the sealed capsule, electronic circuitry located within the sealed capsule for operating the electronic display, the electronic circuitry and the electronic display operative to selectably provide multiple display options, the multiple display options including allowing at least some light from the outside to pass through the electronic display and focusing optics located within the sealed capsule.

Preferably, the focusing optics are arranged for focusing the light from the outside onto the retina.

Preferably, the multiple display options include allowing light from the outside to pass through the entire area of the display. Alternatively, the multiple display options include allowing light from the outside to pass through the display only at certain locations.

In another preferred embodiment, the multiple display options include displaying an image. Additionally, the focusing optics are arranged for focusing the image onto the retina.

Preferably, the focusing optics include a single lens. Alternatively, the focusing optics include multiple lenses.

There is also provided in accordance with another preferred embodiment of the present invention a method for providing a focused input to a retina including implanting a sealed capsule in a user's eye upstream of a retina, the sealed capsule incorporating an electronic display and electronic circuitry for operating the electronic display, the electronic circuitry and the electronic display operative to selectably provide multiple display options, the multiple display options including allowing at least some light from the outside to pass through the electronic display, the multiple display options including displaying an image on the display, selecting one of the multiple display options and focusing at least one of the light from the outside and the image onto the retina.

BRIEF DESCRIPTION OF THE DRAWINGS

The present invention will be understood and appreciated more fully from the following detailed description, taken in conjunction with the drawings in which:

FIGS. 4A and 4B are simplified illustrations of the use of a variable focal length lens arrangement in the implant system of FIGS. 1-3;

FIG. 5 is a simplified exploded view pictorial illustration of an implant forming part of the system of FIGS. 4A & 4B;

DETAILED DESCRIPTION OF PREFERRED EMBODIMENTS

Figure 1:
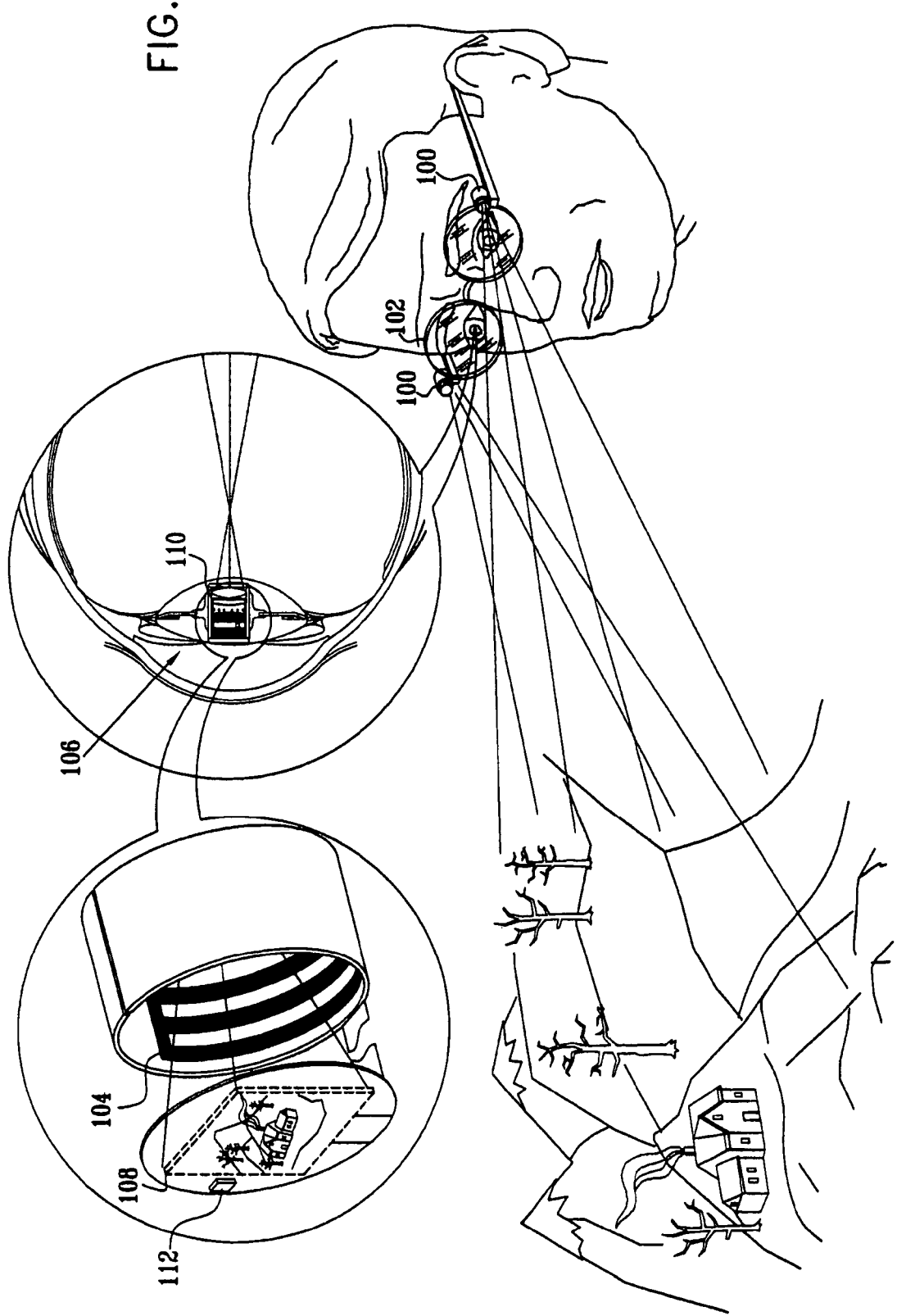
FIG. 1 is a simplified pictorial illustration of an artificial vision system constructed and operative in accordance with a preferred embodiment of the present invention.

Reference is now made to FIG. 1, which is a simplified pictorial illustration of an artificial vision system constructed and operative in accordance with a preferred embodiment of the present invention. As seen in FIG. 1, there is provided an artificial vision system including a real time imaging device, such as a CCD camera. The illustrated embodiment includes both implanted and external imaging devices for the purposes for illustration, it being understood that typically either implanted or external imaging devices will be employed, although both could be used together.

In the illustrated embodiment of FIG. 1, at least one and preferably plural external imaging devices, here designated by reference numeral 100, are typically mounted on a pair of eyeglasses 102, as shown. The external imaging devices 100 view a scene, preferably in stereo. The image information captured by the external imaging devices 100 is transmitted wirelessly, preferably by conventional IR or RF techniques, to electronic circuitry 104 located within a sealed capsule 106 adapted for intraocular placement upstream of a retina. The electronic circuitry 104 is operative to display the captured image as seen by the external imaging devices 100 in real time on an electronic display 108, such as a backlit or self-illuminated LCD display. It is appreciated that electronic circuitry 104 and electronic display 108 may be operative to provide multiple display options, as described further hereinbelow, with reference to FIG. 2.

Focusing optics, typically in the form of a lens assembly 110, in the sealed capsule 106, are operative to image the displayed image onto the retina of a user.

Alternatively or additionally, an implanted imaging device, here designated by reference numeral 112, is located on an outer surface of or interior of each sealed capsule 106. The internal imaging devices 112 view a scene, preferably in stereo. The image information captured by the internal imaging devices 112 is transmitted in a wired or wireless manner, such as by conventional IR or RF techniques, to electronic circuitry 104 located within sealed capsule 106 adapted for intraocular placement upstream of a retina. The electronic circuitry 104 is operative to display the captured image as seen by the internal imaging devices 112 in real time on electronic display 108, such as a backlit or self-illuminated LCD display. Focusing optics, preferably lens assembly 110, in the sealed capsule 106, are operative to image the displayed image onto the retina of a user.

It is noted that the electronic circuitry 104 is located outside an optical path defined between the electronic display 108 and said focusing optics 110.

It is appreciated that, in addition to transmitting an image of a scene, external imaging devices 100 or internal imaging devices 112 may be operative to transmit any other suitable digital information, such as a video image, via electronic circuitry 104 to electronic display 108.

Figure 2:
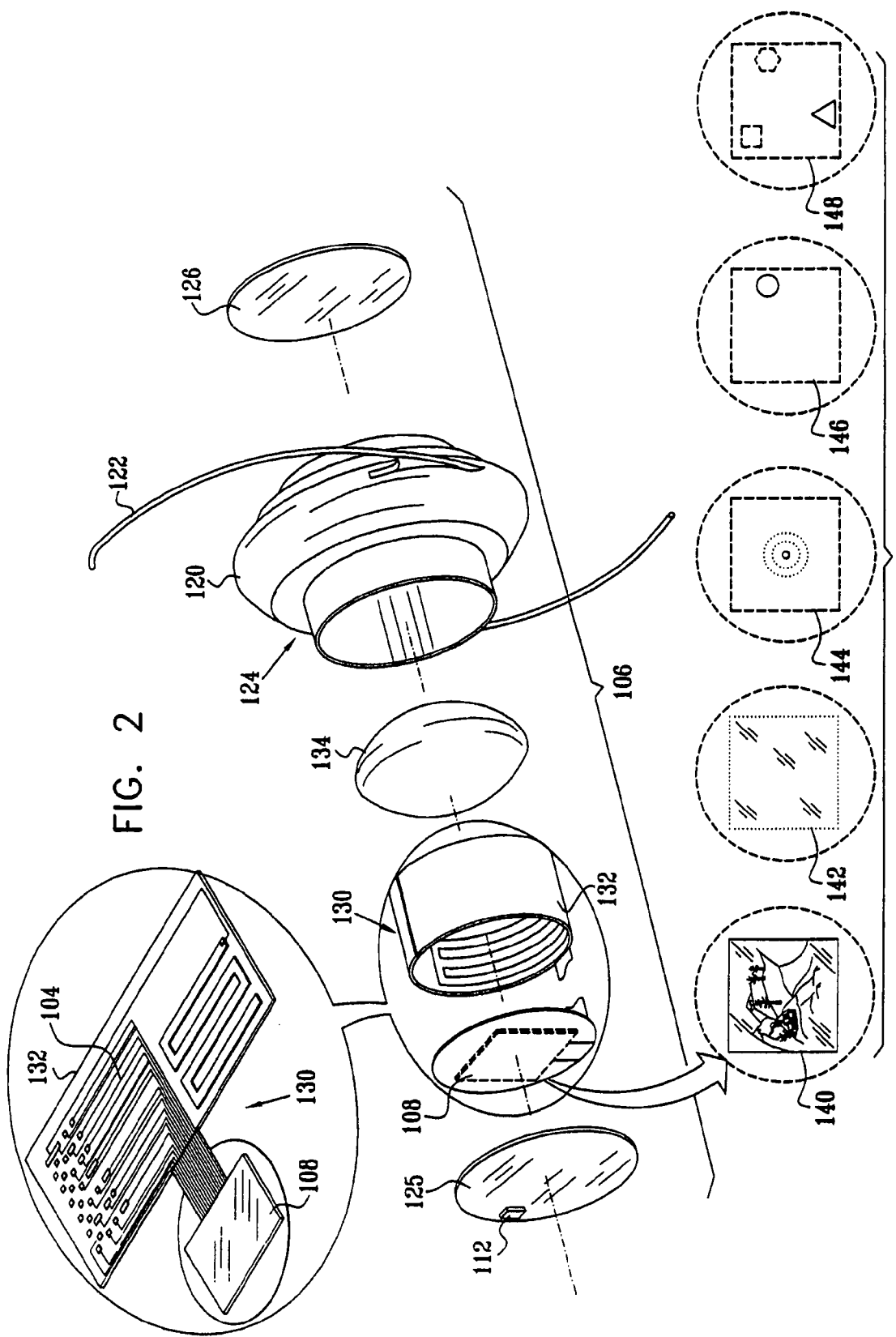
FIG. 2 is a simplified exploded view pictorial illustration of an intraocular implant forming part of the system of FIG. 1.
Figure 3:
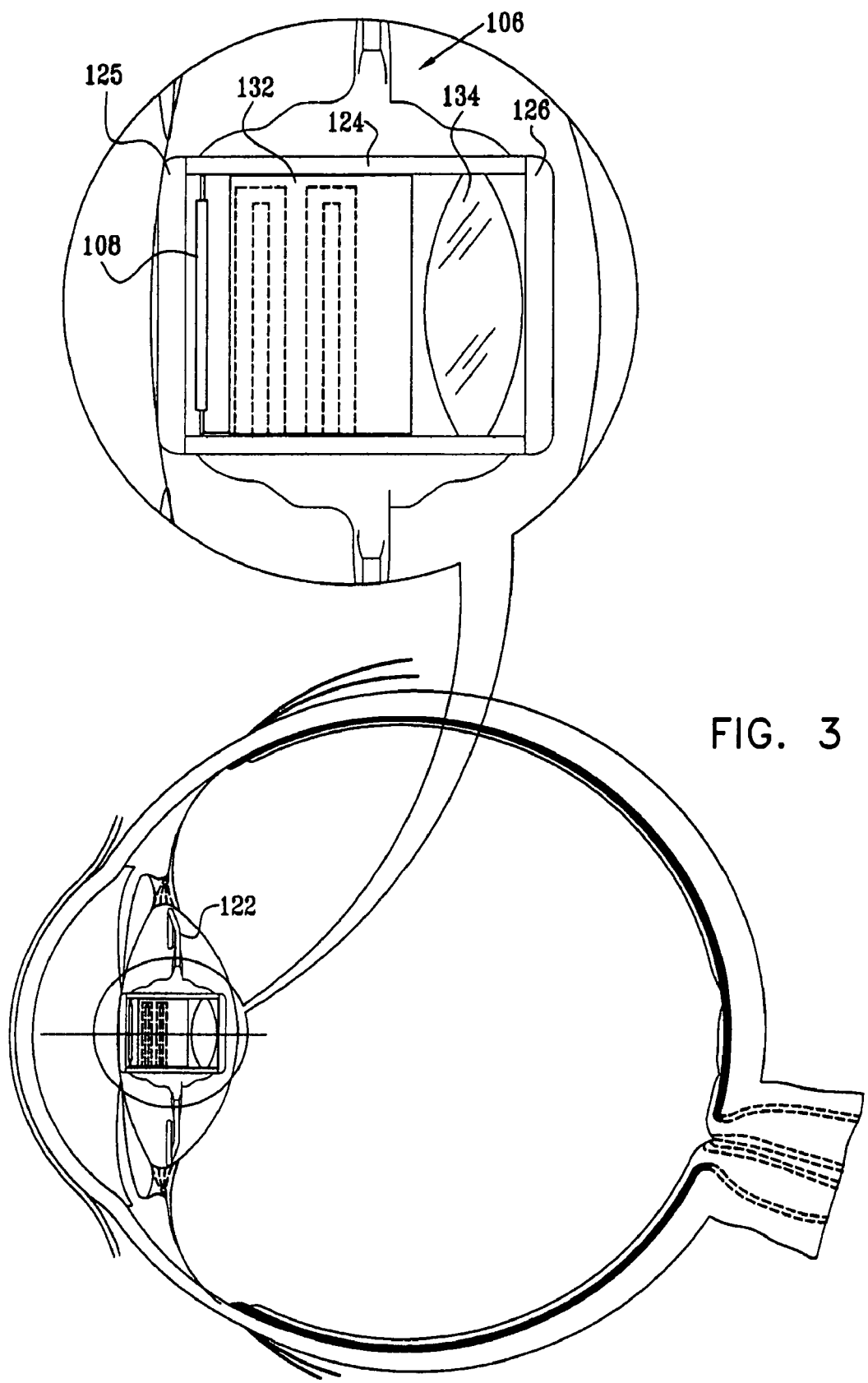
FIG. 3 is a simplified partially sectional side view illustration of the implant of FIG. 2.

Reference is now made to FIGS. 2 and 3, which illustrate some details of the implantable sealed capsule 106 which is shown implanted in a user in FIG. 1. The sealed capsule 106 is defined by an intraocular implant housing 120 having mounting haptics 122 and defining a generally cylindrical capsule body 124. Hermetically sealed to capsule body 124 are a front sealing plate 125 and a back sealing plate 126. Front sealing plate 125 and back sealing plate 126 are transparent. An internal imaging device 112 is shown mounted on an outside surface of front sealing plate 125. Capsules of this type are described in applicants' U.S. Pat. No. 6,569,199 entitled "TELESCOPIC INTRAOCULAR LENS", and U.S. Pat. No. 6,596,026 entitled "TELESCOPIC INTRAOCULAR LENS", the disclosures of which are hereby incorporated by reference.

Preferably disposed within sealed capsule 106 is an electronic circuit and display assembly, here designated by reference numeral 130. Assembly 130 preferably includes electronic display 108 which is coupled to electronic circuitry 104, preferably including a wireless receiver for image data. Display 108 is arranged to lie generally parallel to front sealing plate 125, while electronic circuitry 104 is preferably embodied on a circuit board 132 which is arranged to lie in a cylindrical configuration, peripherally of the optical path between display 108 and back sealing plate 126, so as not to interfere with the optical pathway between the display 108, focusing optics 110 (FIG. 1), here shown as a lens 134, and the user's retina. It is appreciated that even though the embodiment illustrated in FIGS. 2 and 3 shows a single lens 134, focusing optics 110 may also comprise multiple lenses as shown in the embodiment of FIG. 1.

In accordance with a preferred embodiment of the present invention, the electronic circuitry 104 also includes a wireless energy receiver such as a resonant circuit (not shown) and energy storage facilities, such as a rechargeable miniature battery or capacitor (not shown) for wirelessly receiving and storing electrical energy for operating the electrical circuitry and the electronic display.

In the embodiment of FIG. 1, an electrical power source (not shown) external to a user's body, such as a battery mounted in eyeglasses 102, and a suitable energy transmitter, such as a resonant circuit, may be used to transmit operating power to electronic circuit 104 inside sealed capsule 106. Any suitable electrical power source, such as an ultrasonic, electromagnetic and photovoltaic power source, may alternatively be employed interiorly or exteriorly of the capsule.

As seen in FIG. 2, electronic circuitry 104 and electronic display 108 may be operative to provide multiple display options, such as an image captured by external imaging devices 100 or internal imaging devices 112, as described hereinabove with reference to FIG. 1, herein designated by reference numeral 140. Additionally, as designated by reference numeral 142, display 108 may be entirely transparent to allow light from the outside to directly reach the retina.

Alternatively, electronic circuitry 104 and electronic display 108 may be operative to allow light from the outside to pass therethrough only at certain locations by defining at least one transparent aperture in electronic display 108 as shown at reference numerals 144, 146 and 148, respectively, which show different light patterns. Pattern 144 allows light to pass therethrough in a pinhole pattern including pinholes arranged in concentric circles of increasing radii from a center of display 108, while patterns 146 and 148 allow light to pass therethrough in one or more specific, suitably located, regions thereof, where the regions may be of any suitable size and shape.

It is appreciated that patterns 144, 146 and 148, which allow for the selection of light that is allowed to pass through display 108, provide for directing light to preferred retinal locations.

It is further appreciated that the patterns 144, 146 and 148 are shown for illustrative purposes only, and that display 108 may provide for any suitable pattern of light to pass therethrough.

The selection from among the multiple display options is preferably controlled by a user input to electronic circuitry 104, which may be transmitted in a wired or wireless manner, such as by conventional IR or RF techniques. Alternatively, the selection may be automatically controlled.

Reference is now made to FIGS. 4A and 4B, which are simplified illustrations of the use of a variable focal length lens arrangement, usable in the implant system of FIGS. 1-3, as well as in other intraocular implant systems. As seen in FIGS. 4A and 4B, there is provided an intraocular implant system which includes variable focus optics 200 located within a sealed capsule 202 implanted within the eye of a user.

From a consideration of FIGS. 4A and 4B, it can be seen that the relative positioning of at least two lenses 204 and 206 within variable focus optics 200 is variable, preferably in response to an electrical control input, so as to correctly focus onto objects at differing distances.

The relative positioning is preferably produced by an electric displacer, such as a piezoelectric device or a rotary electric motor in response to a wirelessly received viewed object distance indicating input, which may be provided by a conventional range finder or focus resolver, such as employed in conventional automatic focus cameras. Alternatively, a user input may be provided.

Figure 6:
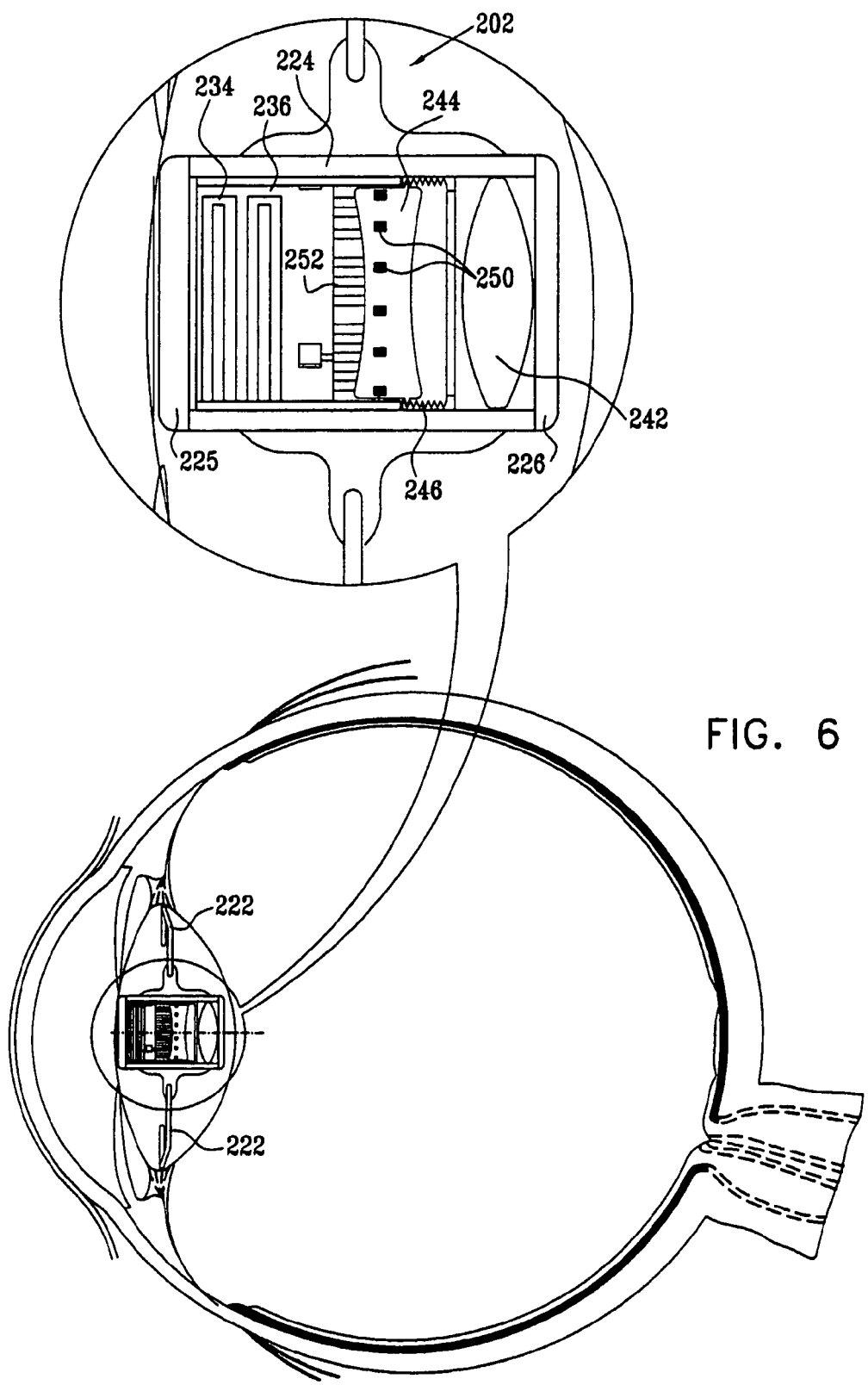
FIG. 6 is a simplified partially sectional side view illustration of the implant of FIG. 5.

Reference is now made to FIGS. 5 and 6, which illustrate some details of the implantable sealed capsule 202 shown implanted in a user in FIGS. 4A and 4B. The sealed capsule 202 is defined by an intraocular implant housing 220 having mounting haptics 222 and defining a generally cylindrical capsule body 224. Hermetically sealed to capsule body 224 are a front sealing plate 225 and a back sealing plate 226. Front sealing plate 225 and back sealing plate 226 are transparent. An internal range finding device 212 is shown mounted on an outside surface of front sealing plate 225. Capsules of this type are described in applicants' U.S. Pat. No. 6,569,199 entitled "TELESCOPIC INTRAOCULAR LENS", and U.S. Pat. No. 6,596,026 entitled "TELESCOPIC INTRAOCULAR LENS", the disclosures of which are hereby incorporated by reference.

An electronic circuit and focus control assembly, here designated by reference numeral 230, is preferably disposed within sealed capsule 202. Assembly 230 preferably includes electronic circuitry 234, preferably including a wireless receiver for receiving ranging information. Electronic circuitry 234 is preferably embodied on a flexible circuit board 236 which is arranged to lie in a cylindrical configuration, peripherally of the optical path through capsule 202 via back sealing plate 226, so as not to interfere with the optical pathway between the viewed scene, via variable focusing optics 240, and the user's retina.

In the illustrated embodiment, the variable focusing optics comprise a fixed lens 242 and a variable position lens 244 which is selectably positionable along its optical axis with respect to fixed lens 242, thus varying the focal length of the variable focusing optics.

In the illustrated embodiment, a threaded mounting 246 is provided for lens 244, and at least one permanent magnet 250, and at least one electromagnetic coil 252 interacting therewith, is preferably provided for selectably threading lens 244 in threaded mounting 246, thus varying its separation from lens 242, in response to control signals from electronic circuitry 234, thereby providing appropriate focusing on a distant viewed object.

It is appreciated that any other suitable mechanism for selectable mutual displacement of lenses 242 and 244 may be employed.

In accordance with a preferred embodiment of the present invention, the electronic circuitry 234 also includes a wireless energy receiver such as a resonant circuit (not shown) and energy storage facilities, such as a rechargeable miniature battery or capacitor (not shown) for wirelessly receiving and storing electrical energy for operating the electrical circuitry 234 and the electromagnetic coil 252.

In one embodiment of the invention, an electrical power source (not shown) external to a user's body, such as a battery mounted in eyeglasses, and a suitable range finder and energy transmitter, such as a resonant circuit, may be used to transmit operating power to electronic circuit 234 inside sealed capsule 202. Any suitable electrical power source, such as an ultrasonic, electromagnetic and photovoltaic power source, may alternatively be employed interiorly or exteriorly of the capsule.

It is appreciated that even though the illustrated embodiment comprises two lenses, any suitable configuration of two or more lenses may also be employed.

Reference is now made to FIGS. 7A-7G, which are simplified sectional illustrations showing examples of alternative implementations of an intraocular lens system employing a sealed capsule 300 implanted in an eye and including at least one negative lens 302 and at least one air bubble 304 and at least one positive lens located outside of the sealed capsule.

Figure 7A:
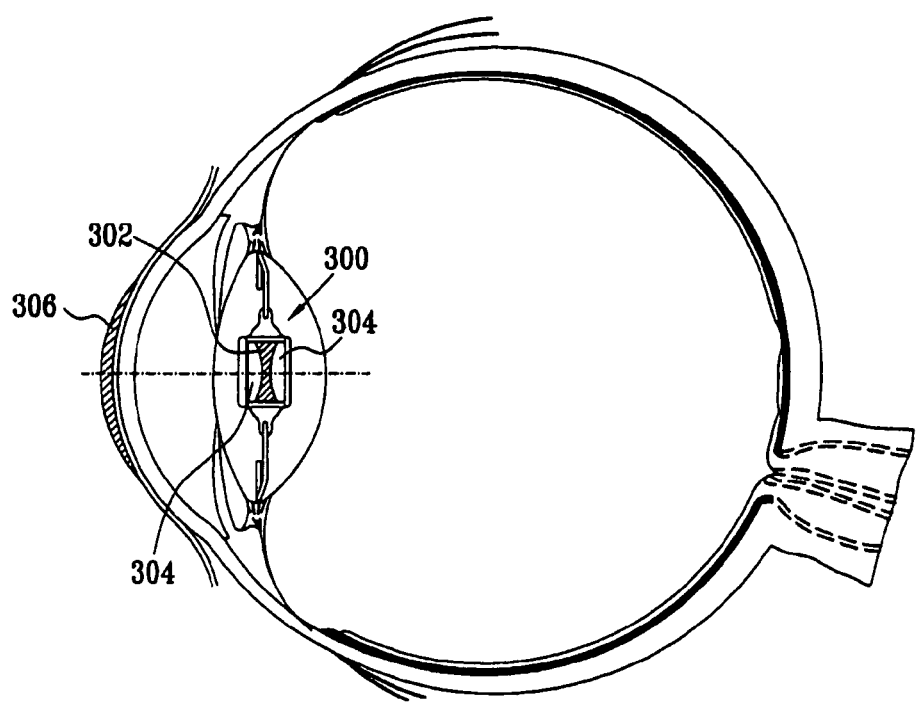
FIGS. 7A-7G are simplified sectional illustrations showing alternative implementations of an intraocular lens system employing a sealed capsule arranged for implantation in an eye and including at least one negative lens and at least one air bubble and at least one positive lens located outside of the sealed capsule.
Figure 7B:
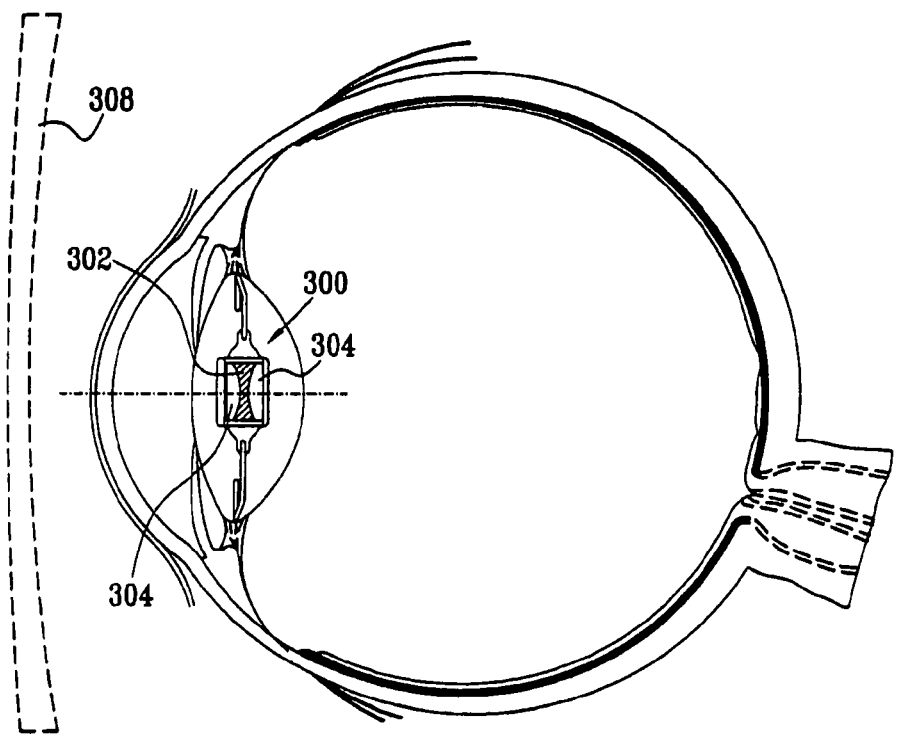
Figure 7C:
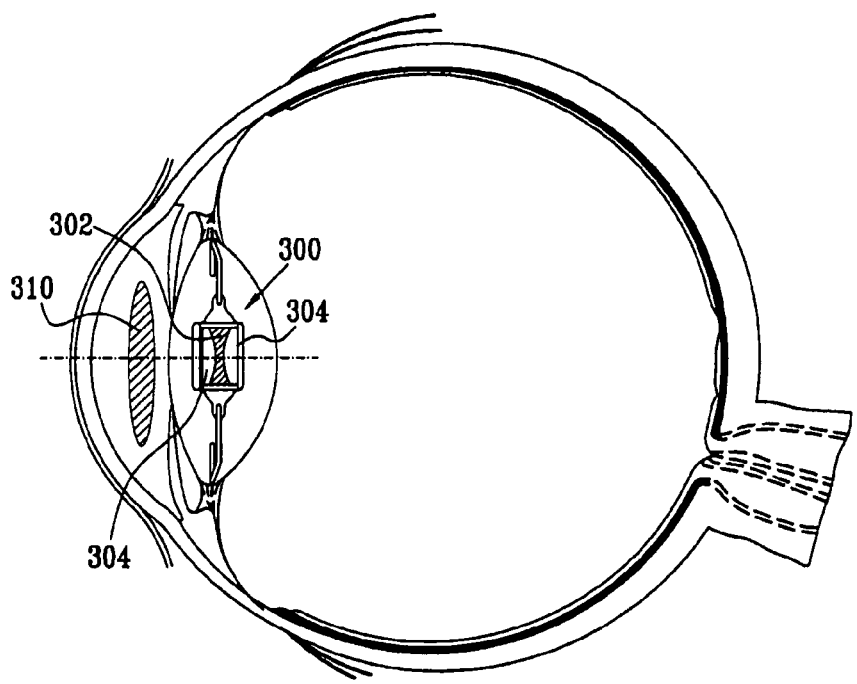

FIG. 7A shows an embodiment where the positive lens is a contact lens 306. In the embodiment of FIG. 7B, the positive lens is an eyeglass lens 308. FIG. 7C illustrates an embodiment where the positive lens is a lens 310 implanted in the anterior chamber of the eye.

Figure 7D:
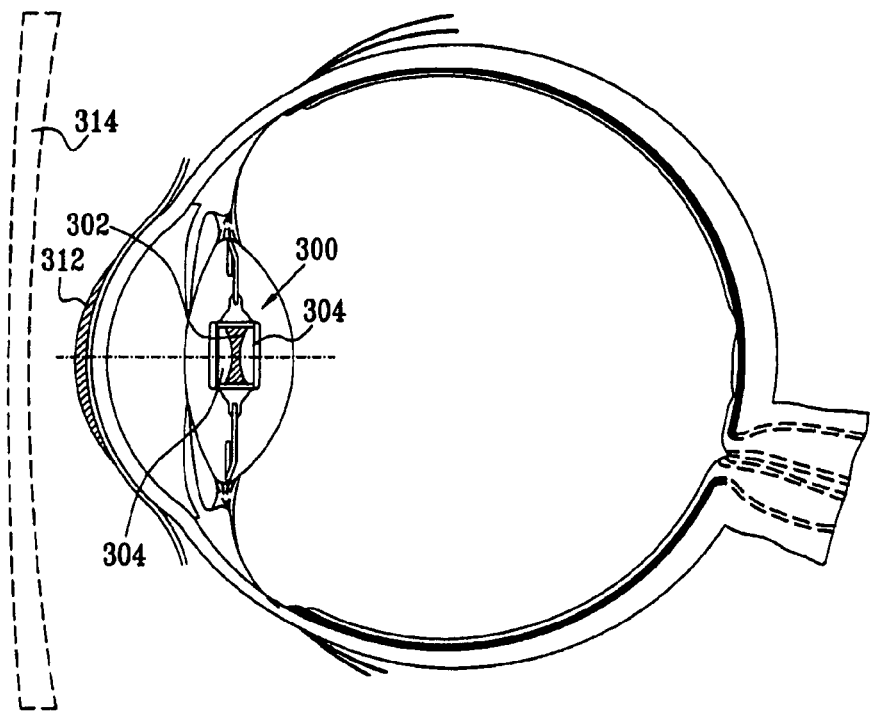
Figure 7E:
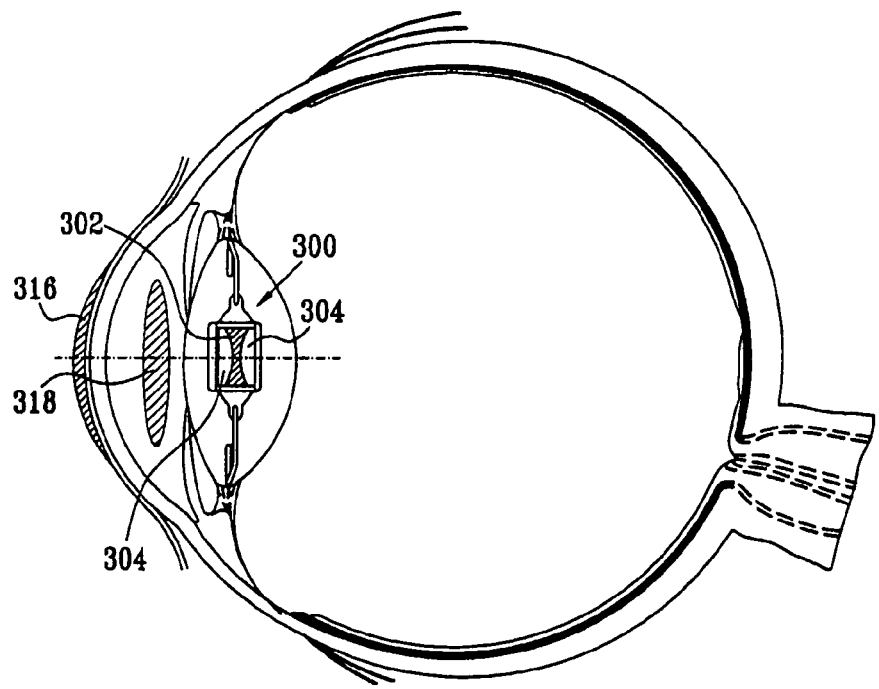
Figure 7F:
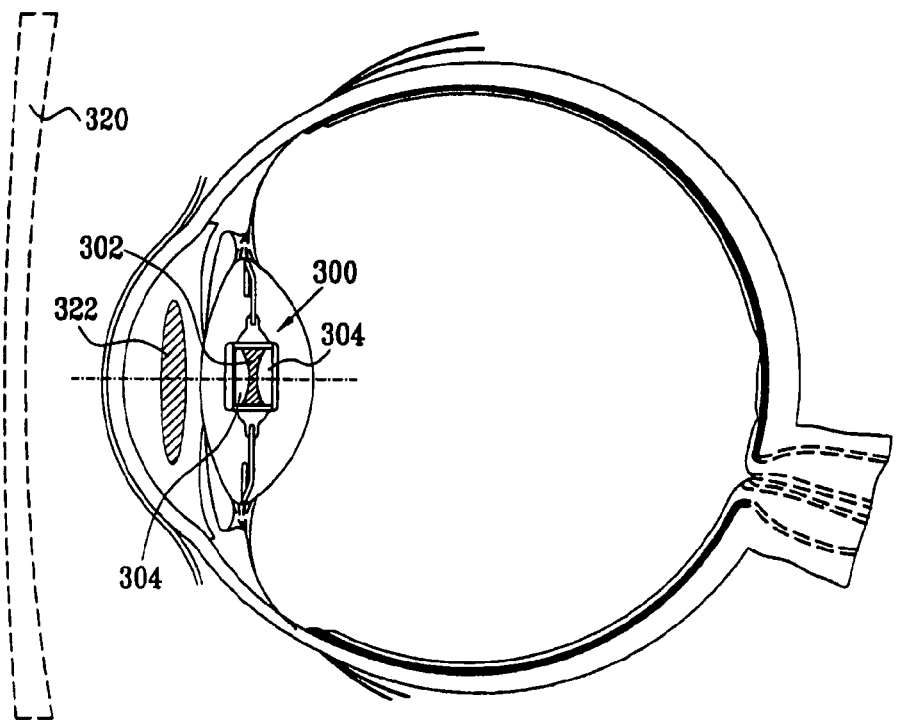

FIG. 7D shows an embodiment where two positive lenses are provided, a contact lens 312 and an eyeglass less 314. In the embodiment of FIG. 7E, two positive lenses are provided, a contact lens 316 and a lens 318 implanted in the anterior chamber of the eye. FIG. 7F illustrates an embodiment where the two positive lenses are an eyeglass lens 320 and a lens 322 implanted in the anterior chamber of the eye.

Figure 7G:
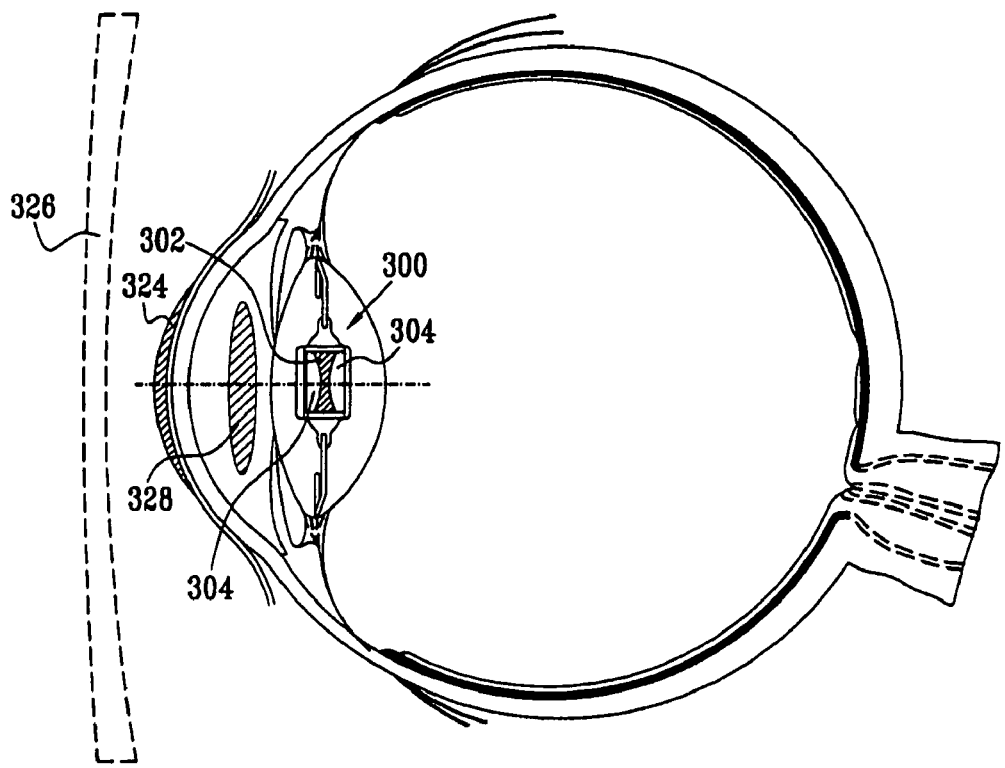

FIG. 7G shows an embodiment where three positive lenses are employed, contact lens 324, eyeglass lens 326 and a lens 328 implanted in the anterior chamber of the eye.

Figure 8:
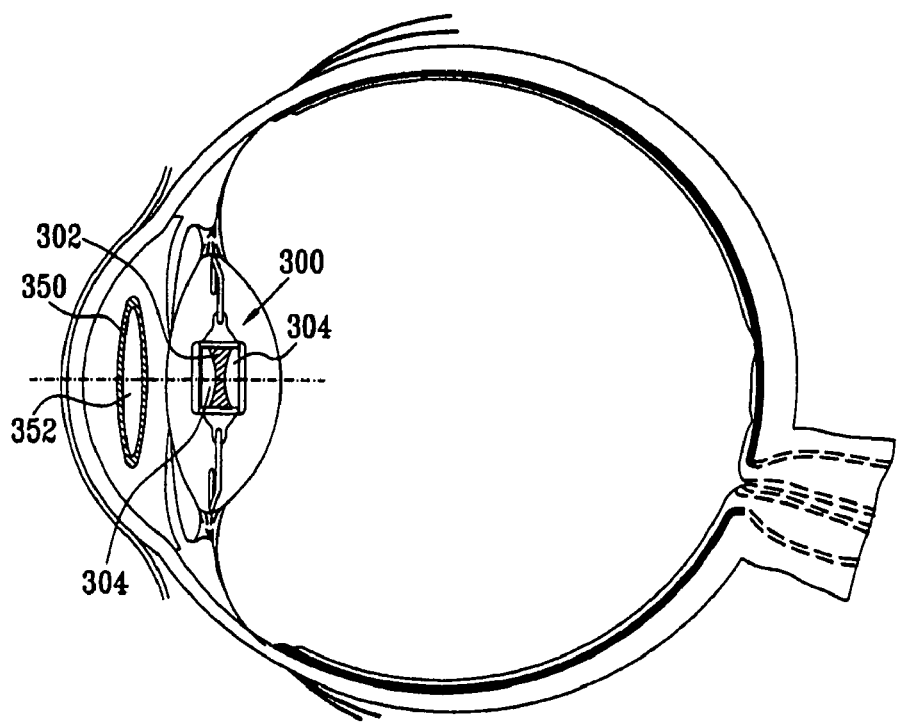
FIG. 8 is a simplified side view sectional illustration of an intraocular lens system of the type shown in FIGS. 7A-7G constructed and operative in accordance with a further embodiment of the present invention.

Reference is now made to FIG. 8, which is a simplified side view sectional illustration of an intraocular lens system of the type shown in FIGS. 7A-7G, constructed and operative in accordance with an additional embodiment of the present invention. In this embodiment, a positive lens 350 is located the anterior chamber of the eye. In the embodiment of FIG. 8, positive lens 350 includes an air capsule 352 to provide higher clarity focusing.

Figure 9C:
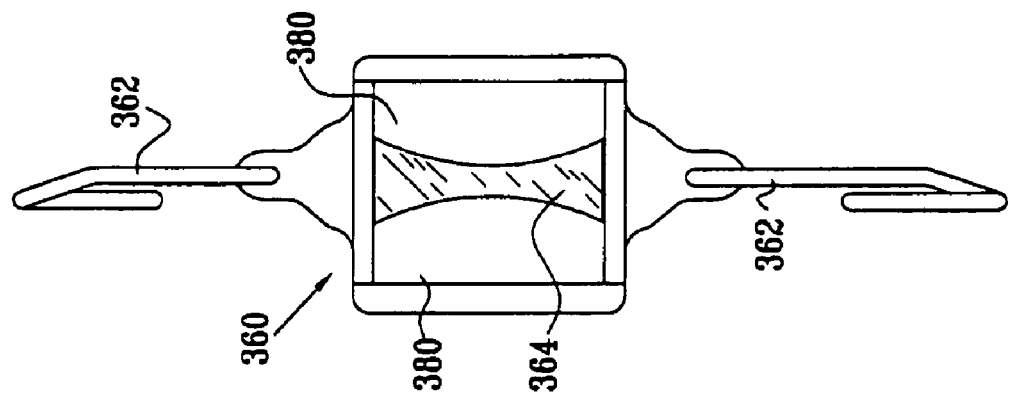
FIGS. 9A-9C are simplified side view illustrations of three examples of implanted sealed capsules of the type employed in the systems of FIGS. 7A-8.
Figure 9B:
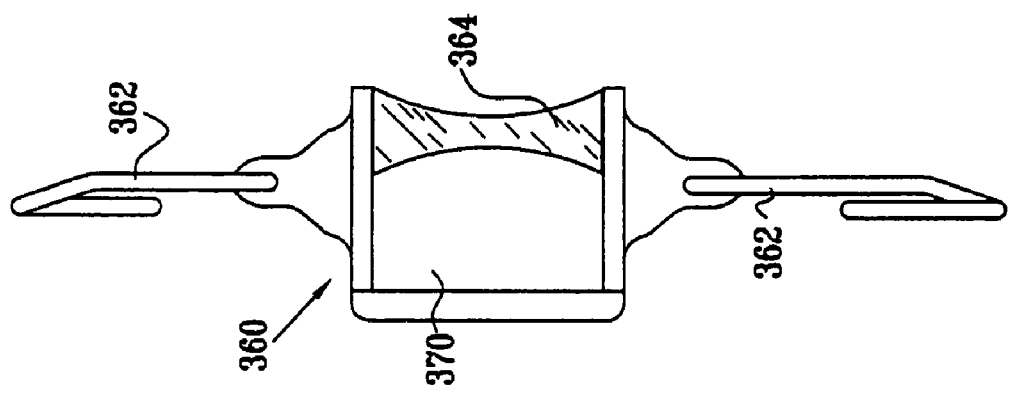
Figure 9A:
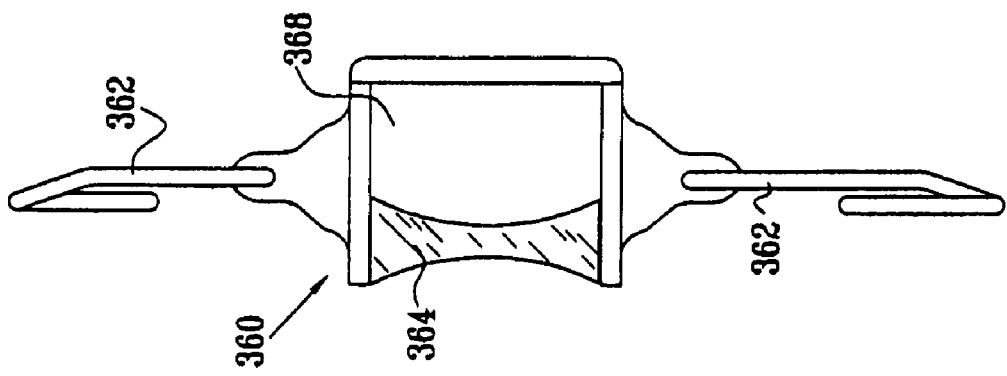

Reference is now made to FIGS. 9A-9C, which are simplified side view illustrations of three examples of implanted sealed capsules of the type employed in the systems of FIGS. 7A-8. It is seen that each of the capsules includes a sealed capsule body 360 and associated mounting haptics 362. Capsules of this type are described in applicants' U.S. Pat. No. 6,569,199 entitled "TELESCOPIC INTRAOCULAR LENS", and U.S. Pat. No. 6,596,026 entitled "TELESCOPIC INTRAOCULAR LENS", the disclosures of which are hereby incorporated by reference. Disposed within the capsule is a negative lens 364.

In the embodiment of FIG. 9A, a relatively large air bubble 368 is disposed rearward of negative lens 364.

In the embodiment of FIG. 9B, a relatively large air bubble 370 is disposed forward of negative lens 364.

In the embodiment of FIG. 9C, air bubbles 380 of approximately the same size are disposed forward and rearward of negative lens 364.

It will be appreciated by persons skilled in the art that the present invention is not limited to what has been particularly shown and described hereinabove. Rather the scope of the present invention includes both combinations and subcombinations of the various features described hereinabove as well as modifications and variations thereof as would occur to a person of skill in the art upon reading the foregoing specification and which are not in the prior art.

The invention claimed is:

1. An intraocular implant cooperating with at least one imaging device operative to view a scene, the intraocular implant comprising:
    a sealed capsule adapted for intraocular placement upstream of a retina, said sealed capsule including:
        electronic circuitry sized and configured for intraocular placement;
        a receiver operative to receive signals representing said scene viewed by said at least one imaging device;
        a transmitter operative to cooperate with said receiver and to transmit said signals to said electronic circuitry;
        an electronic display sized and configured for intraocular placement, and having at least first and second operational display options, said electronic display being operative in said first operational display option, responsive to inputs received from said electronic circuitry, to display an image corresponding to said image of said scene viewed by said imaging device, said electronic display being transparent in said second operational display option to allow at least some light from the outside to pass through said electronic display and to directly reach the retina;

a selection mechanism associated with said electronic circuitry and operative to select between said first operational display option and said second operational display option; and focusing optics arranged for focusing an image appearing on said electronic display onto the retina.

2. An intraocular implant according to claim 1 wherein said focusing optics are arranged for focusing said light from the outside onto the retina.

3. An intraocular implant according to claim 1 and wherein said electronic display is operative, in said second operational display option, to allow light from the outside to pass through the entire area of said display.

4. An intraocular implant according to claim 1 and wherein said electronic display is operative, in said second operational display option, to allow light from the outside to pass through said display only at certain locations.

5. An intraocular implant according to claim 1 and wherein said focusing optics comprise a single lens.

6. An intraocular implant according to claim 1 and wherein said focusing optics comprise multiple lenses.

7. An intraocular implant according to claim 1, and wherein said selection mechanism is operative to select between said first and second operational display options in response to a user input.

8. An intraocular implant according to claim 1, and wherein said at least one imaging device comprises an internal imaging device sized and configured for intraocular placement, which is disposed within said sealed capsule and wherein said receiver is operative to receive said signals representing said scene and to transmit said signals to said electronic circuitry within said sealed capsule.

9. An intraocular implant according to claim 1, and wherein said at least one imaging device comprises an external imaging device which is external to said sealed capsule, the external imaging device cooperating with an external transmitter which is operative to transmit said signals representing said scene to said receiver which is included in said sealed capsule.

10. An intraocular implant according to claim 1 and wherein said electronic circuitry comprises an energy storage facility for storing electrical energy for operating said electronic display.

11. An intraocular implant according to claim 10 and wherein said energy storage facility is selected from a group consisting of a rechargeable miniature battery and a capacitor.

12. An intraocular implant according to claim 1 and wherein said electronic circuitry comprises a wireless energy receiver for wirelessly receiving electrical energy for operating said electronic display.

13. An intraocular implant according to claim 12 and wherein said wireless energy receiver comprises a resonant circuit.

14. An intraocular implant according to claim 12 and wherein said wireless energy receiver is operative to receive said electrical energy for operating said electronic display from a power source which is external to said sealed capsule.

15. An intraocular implant according to claim 14 and wherein said power source which is external to said sealed capsule is selected from a group consisting of an ultrasonic power source, an electromagnetic power source and a photovoltaic power source.

16. An intraocular implant according to claim 1 and wherein said sealed capsule also comprises a power source for operating said electronic circuitry and said electronic display.

17. An intraocular implant according to claim 16 and wherein said power source is selected from a group consisting of an ultrasonic power source, an electromagnetic power source and a photovoltaic power source.

18. An intraocular implant according to claim 1 and wherein said electronic circuitry is embodied on a circuit board which is arranged to lie in a cylindrical configuration peripherally of an optical path between said electronic display and said focusing optics.

19. An intraocular implant according to claim 3 and wherein said focusing optics comprise a single lens.

20. An intraocular implant according to claim 3 and wherein said focusing optics comprise multiple lenses.

21. An intraocular implant according to claim 4 and wherein said focusing optics comprise a single lens.

22. An intraocular implant according to claim 4 and wherein said focusing optics comprise multiple lenses.

* * * * *